(12) United States Patent  
Selker et al.

(10) Patent No.: US 7,489,402 B2
(45) Date of Patent: Feb. 10, 2009

(54) OPTICAL COLLECTION GEOMETRIES FOR PHASE FLUORIMETRY

(75) Inventors: Mark Selker, Los Altos Hills, CA (US); Benjamin Blizard, Mountain View, CA (US); Timothy Johnston, Eureka, CA (US)

(73) Assignee: Finesse Solutions, LLC

( * ) Notice: Subject to any disclaimer, the term of this patent is extended or adjusted under 35 U.S.C. 154(b) by 96 days.

(21) Appl. No.: 11/724,818

(22) Filed: Mar. 16, 2007

(65) Prior Publication Data
US 2008/0170224 A1    Jul. 17, 2008

Related U.S. Application Data

(60) Provisional application No. 60/872,751, filed on Dec. 4, 2006.

(51) Int. Cl.
*G01N 21/64* (2006.01)
(52) U.S. Cl. .................................... 356/417; 250/461.1
(58) Field of Classification Search ................ 356/417; 250/458.1, 459.1, 461.1, 461.2
See application file for complete search history.

(56) References Cited

U.S. PATENT DOCUMENTS 5,281,825 A * 1/1994 Berndt et al. ............ 250/458.1
6,323,495 B1 * 11/2001 Riedel ..................... 250/458.1

* cited by examiner

*Primary Examiner*—F. L Evans
(74) *Attorney, Agent, or Firm*—Herbert Burkard

(57) ABSTRACT

An apparatus and method for the stimulation and collection of fluorescent signals from a target analyte. The apparatus comprises:
 i) a frequency modulated optical source which emits excitation light of a wavelength which will stimulate a target fluorophore to emit a fluorescent signal when illuminated by the excitation light,
 ii) a first optical filter interposed between the optical source and the target fluorophore,
 iii) a second optical filter interposed between the fluorophore and a photo-detector and positioned to receive the emitted fluorescent signal. The beam path of at least one, preferably both, of the excitation light and the fluorescent signal is transmitted substantially through free space. A data processor will normally be used to calculate and record the phase delay between the excitation light and the fluorescent signal.

25 Claims, 9 Drawing Sheets

OPTICAL COLLECTION GEOMETRIES FOR PHASE FLUORIMETRY

RELATED APPLICATIONS

This application claims priority from Provisional Application Ser. No. 60/872,751 filed Dec. 4, 2006, the disclosure of which is incorporated herein by this reference.

FIELD OF THE INVENTION

This invention relates to an improved apparatus and method for the detection of fluorescent signals given off by fluorophores which are used for measuring the concentration of analytes. Such measurement is of particular importance in monitoring bioreactor processes.

BACKGROUND OF THE INVENTION

There is significant interest in the use of analyte sensors based on quenched fluorescence. The list of analytes for which this type of sensor has been suggested includes oxygen, pH, $CO_2$, and glucose. Such sensors have been used in connection with the various processes carried out in bioreactors such as are utilized in the biotechnology, pharmaceutical and food and beverage industries (See e.g., Lakowicz, *Principles of Fluorescence of Spectroscopy*, $3^{rd}$ edition, Springer 2006; R. Narayanaswamy, O. S. Wolfbeis (eds.): *Optical Sensors: Industrial, Environmental and Diagnostic Applications*, Analytical and Bioanalytical Chemistry, Springer (2004), 1618-2642; C. M. McDonagh et al., *Characterization of porosity and response times of sol-gel-derived thin films for oxygen sensor applications*, "J. Non Cryst. Solids, 306, (2002) 138-148.; P. A. Jorge et al, *Application of quantum dots in optical fiber luminescent oxygen sensors*, Applied Optics 45, 16, (2006), 3760-3764; and R. Jaaniso et al., Stability of luminescence decay parameters in oxygen sensitive polymer films doped with Pd-porphyrins, Proceedings of SPIE 5946, (2005), 59460L-1-59460L-10).

Initially, fluorescence based sensors monitored the quenching of fluorescent intensity in the time domain. However, many significant obstacles to reliable performance are encountered. A major issue which arises in using time domain measurement is that it requires sensing a change in the amplitude of the fluorescent signal. This change can be caused by a change in the concentration of the quenching agent (e.g., analyte), but also by a change in the incident power provided by the light source. Also, movement in the position of the fluorescent signal detector can cause an erroneous reading. Even more subtle issues like changes in the properties of the surface of the sensor material (e.g. roughness, index of refraction, and absorbance). Additionally, changes in the position or sensitivity of the photo-detector can lead to drift in the baseline reading.

The terms fluorophore, fluorescent dye, sensor dye and dye are used as equivalents in describing the present invention and are intended to connote an organic, organo-metallic or inorganic compound or mixture of compounds whose upper state fluorescent or phosphorescent lifetime is affected by a target analyte through collisional quenching or Forster type (e.g.: FRET) or dipole mediated energy exchange. In general, any light resulting from optical excitation is referred to as luminescent, whereas the term fluorescent light is frequently used to describe the light that results from singlet to singlet transitions, and the term phosphorescent is used to describe the light resulting from first order dis-allowed triplet to singlet transitions. As used herein the term fluorophore is intended to encompass both fluorescent and phosphorescent materials, and the term fluorescent signal is intended to also encompass a phosphorescent signal. Fluorophores which are capable of detecting a variety of analytes such as $O_2$, pH, $CO_2$ and glucose are known in the art. Recently, significant effort has focused on both actual sensor design and on optimization of fluorophore performance.

With advances in electronics and light sources, the use of information gathering in the frequency domain has become an attractive approach to the measurement of fluorescent signals. Sensors that utilize the phase delay of the fluorescence signal are based on fluorescence lifetime, which is a more intrinsic property of a fluorophore and therefore less likely to be affected by non-analyte induced changes in the environment adjacent to the fluorophore. Phase fluorometric systems work by detecting a change in the phase lag of the emitted fluorescent signal as a function of analyte concentration. In some cases it has been found to be a more efficacious basis for a sensor than monitoring the quenching of fluorescent intensity in the time domain. In general, a shorter (shorter than the emission) wavelength excitation source is modulated by a frequency, f, and a longer wavelength fluorescent signal is emitted at the same modulation frequency, but with a delay in phase. The phase delay is caused by the fact that the energy levels of the fluorescent material have finite time constants associated with them. In many ways, one can use a classical electrical analog to a low pass filter to understand the origin of the delay. The fluorescent states can be thought of as a capacitor which has a capacitance that is a function of the environment. At a given frequency, the phase of the signal passed by the low pass filter is mediated by the capacitor's value. In a similar way, the phase delay between the excitation signal and the emitted fluorescent signal is a function of the analyte concentration. An example of this delay is represented in FIG. 1. (See C. M. McDonagh et al., *Phase fluorimetric dissolved oxygen sensor*, Sensors and Actuators B 74, (2001) 124-130).

In FIG. 1 the excitation signal and the phase lagging fluorescent signal are shown. The relationship describing the phase delay, $\phi$, and its relationship to the modulation frequency, f, and the fluorescent life time $\tau$ is also shown in FIG. 1. $\tau$ will change as the analyte concentration changes, which means that $\phi$ will likewise change as the analyte concentration changes. Methods and suitable data processing equipment which enable one to calculate the phase delay between the excitation signal and the fluorescence signal are known in the art and are described, for example, in Lakowicz, *Principles of Fluorescence of Spectroscopy*, $3^{rd}$ edition, Springer 2006.

A significant problem that can occur with both intensity based and phase fluorimetric based analyte sensors, is photo-degradation of the fluorescent dye. Photo-degradation as used herein refers to the fact that the fluorescent lifetime of a fluorescent dye immobilized in a matrix can change due to extended exposure to light. The absorption of light by photosensitive fluorescent dyes over time can result in the formation of other photo-stable compounds. The electrons present in the photo-stable compounds are no longer able to contribute to the fluorescent nature of the dye, and thereby change the fundamental characteristics of the dye (See Sang-Kyung Lee and Ichiro Okura, *Photostable Optical Oxygen Sensing Material: Platinum Tetrakis (pentafluorphenyl) porphryin Immobilized in Polystyrene*, Analytical Communications, 34, (1997), 185-188; K. Oige et al, *Effect of long-term aging oxygen sensitivity of luminescent Pd-tetrahenylporphrin/PMMA films*, Sensors and Actuators B 106 (2005) 424-430.

Most currently used fluorophores absorb in the blue-green region of the visible spectrum. One significant consequence of this fact is that ambient light, especially sunlight, can change the material properties of the fluorophore and therefore significantly affect its behavior as a sensing element. If the rate of this change is rapid, the fluorophore's reliability as a sensing element will be adversely affected. Also, if the material properties of the fluorophore change during use, the baseline reading of the analyte concentration will likewise change erroneously during use. Such effects can lead to poor accuracy, low precision, and high drift. Especially for bioprocess applications, stringent performance requirements are placed on accuracy, precision and drift, as a result of which currently known fluorescent-based sensors do not fully meet many bioprocess requirements. Furthermore, such effects will make the storage requirements for fluorophores, especially those for use in disposable sensors, more onerous, as they will age during storage if exposed to ambient light.

In general, it is known that the rate at which changes to a fluorophore occur is directly proportional to the intensity of the excitation light and exposure to ambient light (as well as analyte concentration). One method of reducing deleterious effects is to reduce the exposure of the fluorescent dye to both stray light, and also to reduce the required amount of excitation light. The fluorescent dye can generally be relatively easily shielded from the stray light; however, reducing the required amount of excitation light is a much greater challenge. The present invention provides a major advance in terms of reducing the amount of required excitation light and avoiding degradation of the fluorophore while nevertheless ensuring that the amount of fluorescent signal which reaches the detector is sufficient The construction of prior art fluorescence based sensors has generally favored using fiber-optic based illumination and collection geometries. Such a prior art design is shown in FIG. 2. In FIG. 2, 1 is the excitation LED, 2 is an optical filter which tailors the excitation spectrum such that it is matched to the absorption wavelength of the analyte sensitive dye 6. 3 is a fiber-optical coupler which allows the excitation light to travel into the common delivery/collection fiber 4, while allowing the fluorescent signal to simultaneously travel in the opposite direction. The fluorescent signal is then passed through optical filter 7 so that only the fluorescent signal reaches optical detector 8. 5 is a set of coupling optics (optional) to help increase collection and delivery of light from and to the dye, respectively. An obvious aspect of the system pictured in FIG. 2 is that the excitation light is remotely filtered and coupled into a single fiber, while the collected fluorescent signal is delivered to a photo-detector which is also located remotely from the dye. This allows a system where the optical sources and coupling all occur at the same location as the data processing electronics. While this simplifies some of the design and implementation issues and allows the use of fiber-optic for both delivery of the excitation light and collection of the fluorescence signal from a remote location, it is also limiting in several ways. First, the fiber's ability to withstand bending and other mechanical perturbation is limited. Leakage of both illumination light and signal light caused by bending the fiber or fiber bundle results in the excitation light actually impinging on the fluorophore being of lower than optimal power, and loss of the collected fluorescent signal can significantly reduce the signal to noise ratio. The use of multiple fibers or fiber bundles can help, but dramatically increases the cost and complexity of the system. The collection of the fluorescent signal is often the most vexing problem, and the ability of the fiber (or fiber bundle) to collect light is limited so that most systems of this type collect substantially less than 10% of the light emitted by the fluorophore. In fact, the maximum amount of the emitted fluorescence signal which any optic fiber based system can collect is substantially less than 50% unless the spot is deposited directly on the core of the fiber. The present invention overcomes the significant disadvantage of using optical fiber and enables the collection of greater than 50% and indeed can actually achieve almost 100% collection from an extended fluorescent source. Specifically by an "extended source", we mean a source of greater than 1 mm in diameter that behaves as a Lambertian emitter. When the dye fluoresces it emits into all space, (i.e. over a hemisphere) so that approximately half of the light can be collected from the half plane. In general, a fluorescent dye layer that is thicker than a few tens of wavelengths will emit light as a Lambertian source into this half plane with an intensity that is proportional to $\cos[\theta]$ of the angle at which it is viewed, as is shown in FIG. 3. (See http://en.wikipedia.org/wiki/Image:LambertCosineLaw1.png).

In FIG. 3, I is the intensity, $\theta$ is the angle from the normal which the radiation is viewed, dA is a differential element of area, and $d\Omega$ is a differential element of solid angle. By looking at the emission pattern shown in FIG. 3, it is clear that a fiber's ability to collect light from such a source is limited. As the area of the source, A, increases, the fiber's collection efficiency is further reduced.

In general, fibers used in sensors have a circular collection area with a diameter of ~1 mm or even less. Additionally, the fibers can generally only collect light that hits the fiber with an angle $\sim \leq \pm 30$ degrees. The definition of a Lambertian source, in contrast, stipulates that the emission angle is $\pm 90$ degrees, which is a mismatch to a typical fiber which can collect at most 30% of the emitted light, and frequently significantly less. It should also be noted that the fluorescent dyes are generally deposited in a 2-5 mm diameter circular spot which means that the 30% of light collected will be further reduced by another factor of 9 to 25, leading to a collection efficiency ranging from a little over 1% to at most 10%. Our invention, which utilizes free space transmission of the majority of at least one of the excitation light and the fluorescence signal (and preferably both) and in all cases avoids the use of fiber-optic, thereby achieves dramatically superior collection efficiency. As above-indicated, the present invention enables the collection of greater than 50% of the photons emitted by the fluorophore, and indeed can actually achieve almost 100% collection efficiency from extended fluorescent sources.

In order to quantify the mismatch between the Lambertian emission of a fluorescent dye and the collection efficiency of a typical optical fiber as compared to the collection efficiency achievable by the present invention, it is necessary to consider a concept referred to as brightness. The quantity shown in Equation 1, which is called brightness, can be shown from fundamental thermodynamics to be a conserved quantity. (See Ross, McCluney, *Introduction to Radiometry and Photometry*).

$$\frac{\text{Power}}{\text{Solid Angle} \times \text{Area}} \qquad \text{Equation 1}$$

The denominator, which is the product of the solid angle radiated to/from and the area radiated to/from, is called étendue. This concept means that it is never possible to take a source having a given power and étendue and make it brighter. Likewise, it is not possible to couple into a smaller area or smaller angular acceptance without losing power. With the concept of conservation of brightness in mind, consider a fluorescent source having a 5 mm diameter (area=$\pi(2.5)^2$ mm$^2$) radiating into a half plane. Equation 1 tells us that the majority of the radiated light cannot be collected by a fiber with a 1 mm diameter (area=π(0.5)² mm²) and one third of the collection solid angle. Taking the ratio of the area of the 5 mm diameter fluorescent spot to the area of the 1 mm diameter fiber we have:

$$\frac{\text{emission area}}{\text{collection area}} = \frac{\pi \, 2.5^2}{\pi \, 0.5^2} = 25 \qquad \text{Equation 2}$$

Equation 2 shows that the area factor alone in Equation 1 causes a decrease in collection efficiency by a factor of 25 for a typical fiber. If one also accounts for the angular distribution of the Lambertian source emitting into a half sphere compared to the fiber's angular limited collection ability, we have a source which has an étendue that is approximately 75 times that of the fiber. It would be exactly a factor of 75 only if the extended source were uniform and not Lambertian with the same solid angle limits. In order for brightness to be conserved, and assuming a uniform illumination source, the difference will be made up by a factor of 75 loss in power coupled into the optical fiber. If the resulting signal after the photo-detector does not result in a sufficient signal to noise ratio in the detection electronics, the excitation source power will need to be increased accordingly, or the sensor will not accurately measure the phase angle. This increased excitation power, in turn, results in an increased rate of photo-degradation of the dye. Additionally, if the collection fiber is bent beyond its ability to guide light so that there is leakage of the signal, the excitation light will also need to be increased to make up for this loss. If the loss in fluorescent signal power causes a significant decrease in the signal to noise ratio, the increased illumination power results in a significantly increased rate of photo-degradation of the fluorophore. Our design does not use fibers, so it is not susceptible to this issue. Additionally, because of the enhanced collection efficiency of the apparatus of the present invention, in many instances we are able to effectively utilize excitation light sources which deliver intensities<1 μW/mm² and not realize the same photo-degradation rate provided by a fiber based source delivering~10 μW/mm².

DESCRIPTION OF THE INVENTION

Figure 1:
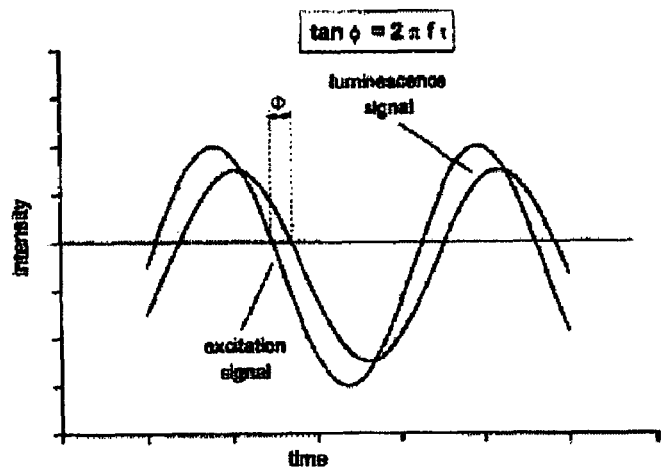
FIG. 1 is a graph showing the excitation signal and the phase lagging fluorescent signal for a prior art phase fluorimetric dissolved oxygen sensor
Figure 2:
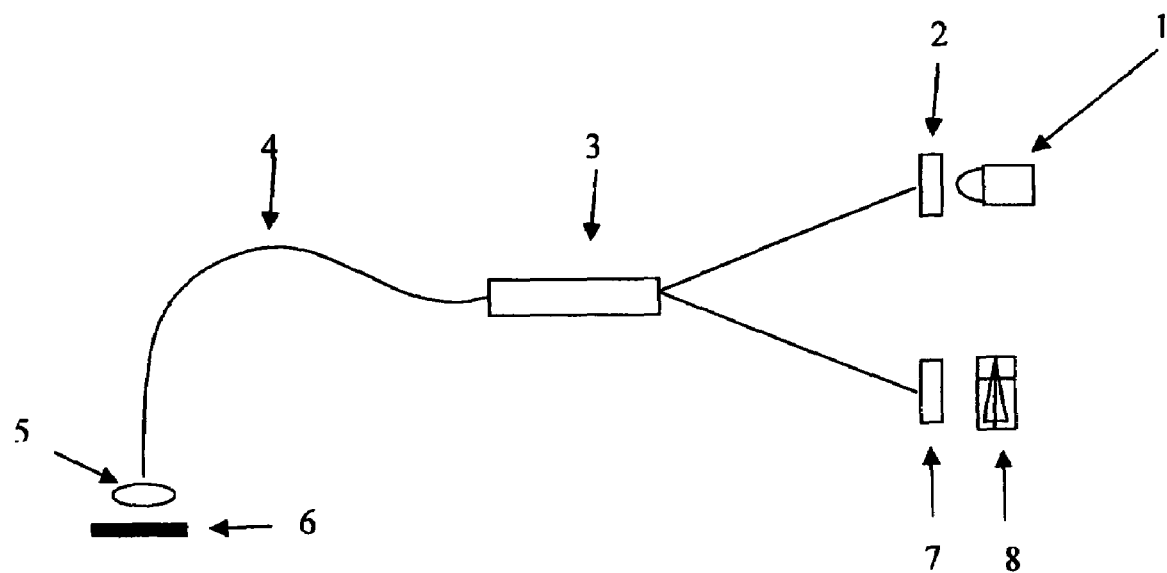
FIG. 2 shows a prior art design for a fluorescence sensor utilizing fiber-optic based illumination and collection geometries.
Figure 3:
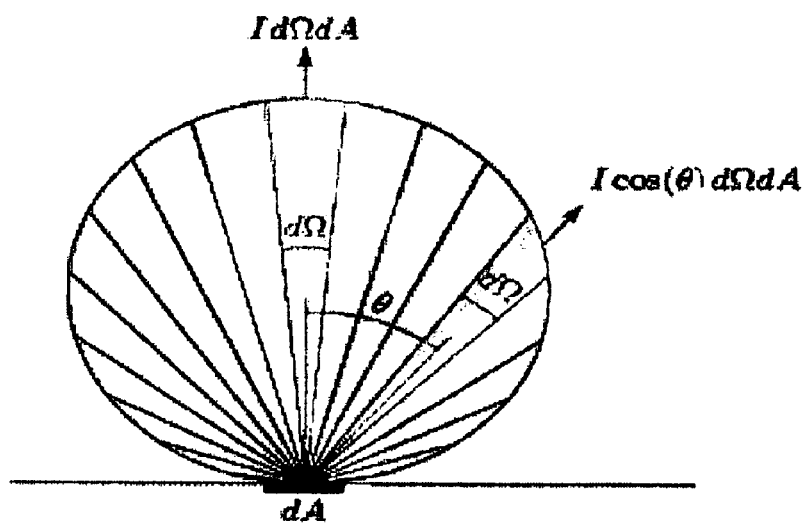
FIG. 3 shows that a dye layer that is thicker than a few tens of its emission wavelength will emit light as a Lambertian source with an intensity that is proportional to Cos [θ] of the angle at which it is viewed.

We have developed an optical collection system and method for the detection of fluorescent signals which does not utilize optic fiber or fiber bundle transmission of either the illumination (excitation) light or the fluorescent signal and thereby avoids many of the inherent shortcomings of prior art designs. We have found an advantageous way to minimize the loss between the emitted fluorescent light (fluorescent signal) and the photo-detector, i.e., maximize the collection efficiency, by eliminating the use of fibers or fiber bundles for the collection of the emitted fluorescent light. Our system design, which utilizes free space transmission of at least one of the excitation light and fluorescent signal, and preferably both, permits use of a larger area of fluorophore (spot size) e.g., a diameter of at least 1 mm and frequently 3 mm or even larger, since its ability to collect the fluorescent signal is not limited by the numerical aperture or core size of an optical fiber (currently about 1 mm maximum diameter). Although we have used the term diameter in connection with the description of the fluorophore spot it is to be understood that for reasons of achieving uniformity of the intensity of the illumination source on the fluorophore, the fluorophore will preferably be substantially circular in shape. However, this is not a requirement of the present invention and the benefits of our design apply equally well to different fluorophore spot shapes (e.g.: square, hexagon, etc.) or natural fluorescence by the target analyte itself. replaces a fluorophore spot. By describing a spot as having diameter of at least 1 mm we intend to encompass spots having a surface area of at least π mm². Our design preferably utilizes both brightness conserving optical elements and free space transmission, and can thereby achieve the beneficial result that substantially all of the photons emitted by the fluorophore are collected by the photo-detector. However, elements that do not strictly conserve brightness can also be used. Specifically, it is possible to design systems in accordance with the present invention using a lens in an optimized geometry with the spot such that the percentage of the emitted light collected (i.e., in excess of 50%) far exceeds that possible with prior art fiber based systems or systems where no attention is paid to the placement of the spot and the detector. Additionally, this arrangement allows the use of a larger area spot. The larger area means that with the same intensity excitation light, a larger number of photons can be collected. Therefore, using with the same or lower intensity to what is used with a fiber optic based system we can simultaneously achieve an equal or lower photo-degradation rate and an equal or higher signal level to the aforementioned fiber optic system. With our system we have achieved excellent results even when the excitation light has an intensity of no greater than about 3 $\mu W/mm^2$.

Under normal conditions with our invention the photon transmission efficiency of both the excitation light and the fluorophore emission approach 100%. Prior art systems can never even theoretically approach this efficiency. Our system is therefore superior both in terms of accuracy and enhanced service life due to, among other advantages, a reduced susceptibility to photo-degradation of the fluorophore as a result of the substantially uniform illumination of the entire fluorophore surface. Our optical system therefore collects light more effectively from extended sources such as a Lambertian source. Furthermore, because our collection system can be physically located very close to the fluorescing area, our system is both effective and economical to implement.

Figure 4:
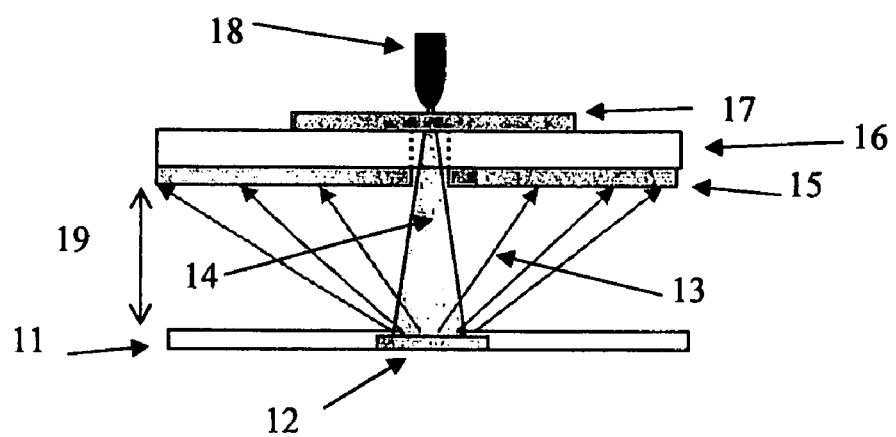
FIG. 4 shows a side view of a first collection system in accordance with the present invention. Collection systems in accordance with the present invention eliminate the use of optical fibers or fiber bundles for both the delivery of the excitation light and the collection of the emitted fluorescent light.

The side view of a collection system in accordance with the present invention is shown in a side view in FIG. 4 where 11 is a substrate on which the fluorophore is placed. In the embodiment shown in FIG. 10, the collection system of FIG. 4 is utilized in a full system. As shown in FIG. 4 and in the subsequent Figures illustrative of the present invention, whether or not the substrate is disposable, the substrate to which the fluorophore is affixed will preferably be a biocompatible, high optical transparency, moldable, animal-derived-product-free, and FDA Class VI compliant material, or alternatively, a sterilizable, non-reactive rigid material such as 316L stainless steel. Compliant materials that meet these criteria include, but are not limited to, varieties of polycarbonate, polysulfone, and acrylic polymers and also cyclo-olefin polymers such as Zeonor and Zeonex. In FIG. 4, 12 is the sensor dye, 13 is the Lambertian fluorescent signal, and 14 is the excitation light. The excitation light is provided by a suitable source such as an LED 18 and is passed through optical filter 17 (preferably a band pass filter) which shapes the spectrum of the illumination light source, thereby providing excitation light in the preferred absorption region of the sensor dye. There are often multiple regions where the dye absorbs but our design limits the energy of the photon and avoids leakage into the photo-detector. Suitable filters are known to the skilled artworker and include a multi-layer dielectric or absorptive glass filter or a filter combining both elements. After passing through the filter, the excitation light is sent through a hole in photo-detector, 16. The hole in detector 16 in FIG. 4 is shown at the center of the detector, but the hole can be anywhere in the photo-detector or alternatively can be a notch in the detector circumference. This hole in the photo-detector allows direct illumination of the fluorescent dye by the excitation light and has the advantage of providing substantially uniform illumination over the entire dye surface, which minimizes local photo-degradation due to hot spots and allows any photo-degradation that does occur to be substantially uniform over the entire area of the fluorescent material. The fluorescent signal passes through a filter, 15, which removes all light of a wavelength other than that of the fluorescence light before it impinges upon the photo-detector. Suitable filters are known to the skilled artworker and include a multi-layer dielectric or absorptive glass filter or a filter combining both elements. Suitable photo-detectors are also known to those skilled in the art and can, for example, be a PIN photodiode, an avalanche photodiode, or a photomultiplier tube. The basic requirement for the photo-detector is that it have adequate sensitivity at the fluorescence wavelength so that the output signal the detector produces has a sufficiently high signal-to-noise ratio that it can be electronically amplified or transmitted to the electrical circuits that will process (and if desired display and/or record the data). In the information processing step that follows, the phase delay of the fluorescence with respect to the excitation light is calculated. This phase delay can be calibrated, for example, by using known concentrations of the target analyte to correlate with the measured phase delays and thereby provides a measure of the concentration of the analyte under study. See Lakowicz, *Principles of Fluorescence of Spectroscopy*, $3^{rd}$ edition, Springer 2006.

The system shown in FIG. 4 enables the capture of a large percentage of the emitted fluorescence signal. The collection efficiency is primarily determined by the distance 19, between the detector and the emitting fluorophore, and by the size of the detector. The collection efficiency can approach almost 100%, depending on the precise geometry and the index of refraction of the materials used. As previously indicated, such collection efficiency is well beyond the collection efficiency which is even theoretically achievable with prior art designs. The optical system will preferably have the detector and its optical filter as physically proximate to the fluorescence emitter (fluorophore) as possible.

Figure 5:
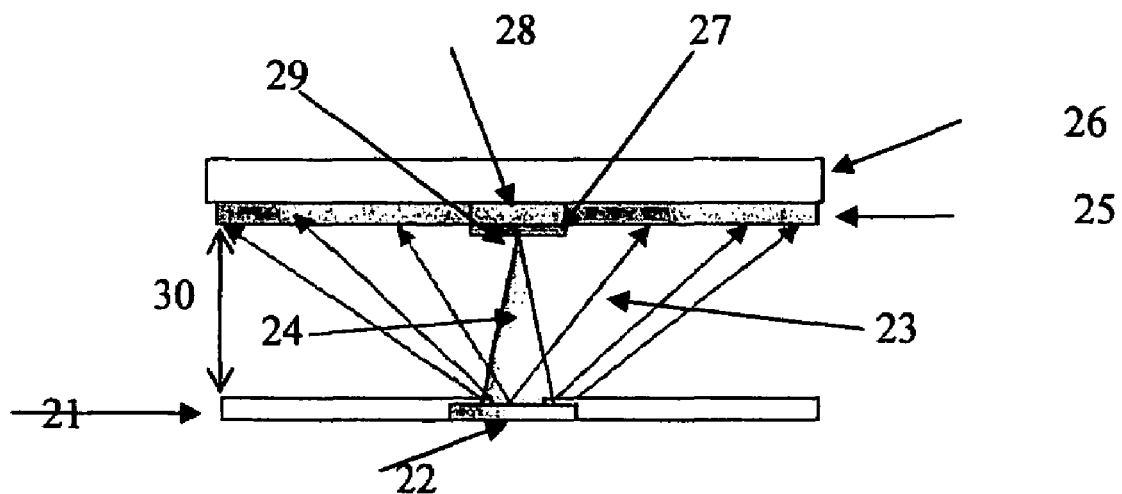
FIG. 5 shows an alternative embodiment of a collection system in accordance with the present invention.

Another variation of the design of the present invention is shown in FIG. 5. Although a generally similar geometry which utilized near infra-red sources and detectors has been applied to microscopes, in the prior art microscope design, the optical source and photo-detector were made from the same semiconductor material (gallium arsenide) and thus could be fabricated on a common substrate.

(See http://harrisfiles.stanford.edu/levipub/Bio_fluorescence_sensor_SPRC_03.PDF]). In the visible spectral region, as is preferably used for fluorescence detection, this prior art architecture would not be usable, since for fluorescence detection the preferred optical source materials are GaN-based, while silicon based photo-detectors are preferred. For fluorimetry applications, a design in accordance with the present invention is shown in FIG. 5. In the embodiment of FIG. 5, 21 is compliant polymeric material on which a disk 22 of the fluorescent dye is affixed, 23 is the fluorescent emission, 24 is the excitation light, and 25 is an optical filter that ensures that the light reaching the photo-detector 26 contains only the fluorescent signal. An important difference between this design and the design shown in FIG. 4, is that in FIG. 5 the excitation source 28 (e.g.: LED, VCSEL, or edge emitting semiconductor laser) is mounted directly on the photo-detector. The optical source 28 has its spectrum tailored by an appropriate filter 27 so that the light impinging on the dye is matched to the optimal part of the absorption spectrum and no undesired light (e.g. ultraviolet (UV) light which can accelerate photo-degradation) can impinge on the dye. However, it should be noted that although for most applications the preferred illumination light will be in the visible range, for certain fluorophores the wavelength of the illuminating light source will be in the near UV. The apparatus and method of the present invention are suitable for use with both visible and UV illumination sources. The filtered excitation light can also be shaped to spatially match the dye spot size by an appropriate optical system such as lens 29. As in the design shown in FIG. 4, the distance 30 between the given size photo-detector and a given size dye spot affects the collection efficiency. A difference between the embodiment of FIG. 5 and that shown in FIG. 4 is that the excitation source is mounted directly on the photodiode.

Figure 6:
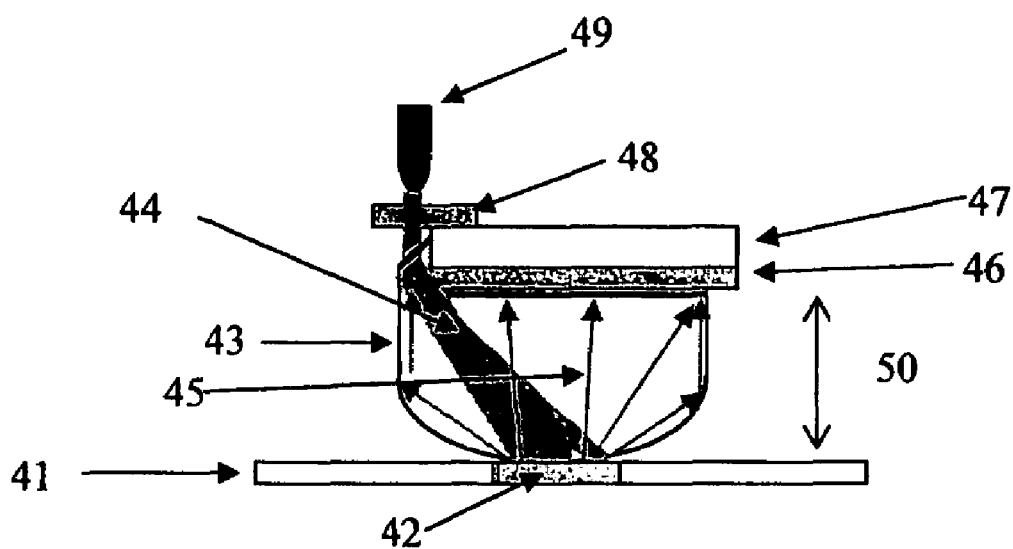
FIG. 6 shows an embodiment of the present invention which includes additional optical elements such as in this embodiment, a curved parabolic collimator ("CPC") which we have found enhances the collection efficiency of the fluorescent signal.

In the embodiments shown in both FIGS. 4 and 5, no additional collection optics are shown. However, it is also possible to non-fiber-optic based optical elements to enhance the collection efficiency of the fluorescent signal. Such an alternative embodiment is depicted in FIG. 6, where 41 is the substrate material, and 42 is the fluorescent dye mounted thereon. The collection of the fluorescent signal, 45, is accomplished with a curved parabolic collimator ("CPC"), shown as 43 (See Welford and Winston in *Nonimaging Optics*, by: Roland Winston, Juan C. Mintano, Pablo Benitez, with contributions by Narkis Shatz and John C. Bortz, Elsevier Academic Press, 2005). This optical collection device can be designed using a curved outside wall to reflect the light. Since the material of the CPC has a refractive index higher than that of air, it is possible design the curvature of the CPC such that fluorescent light hits the walls of the CPC at angles of incidence above the critical angle and therefore the light undergoes total internal reflection. These design principles are outlined in the reference given above. In FIG. 6, the excitation light 44 comes from an LED or other suitable optical source 49, and is sent through a hole in the photo-detector and the optical filter. This hole can be physically located either in the center of the photodetector, or off-center. The design shown in FIG. 6 uses an off-center arrangement and also utilizes a shaped wedge to refract the light at an angle such that it will illuminate the fluorophore. As in the other embodiments of the present invention the light source is preferably sent through an optical filter 48 to condition the light by removing undesired wavelengths. The fluorescent signal is also sent through a filter 46, which prevents both stray light, and also reflected excitation light, from impinging upon the detector. A CPC is particularly useful when it is difficult because of other design requirements to minimize the distance 50 between the detector and the emitting fluorophore, because the CPC can provide very close to 100% collection efficiency, even if the distance from the fluorophore to the photo-detector is relatively large. The CPC situation differs from a free space propagation situation where the detector is preferably within a few millimeters of a fluorescent spot which is normally at least 1 and preferably 2-5 mm in diameter. The system shown in FIG. 6 can also be configured so that the illumination comes through a hole in the center of the photo-detector, or alternatively through a notch in the edge of the photo-detector.

Figure 7:
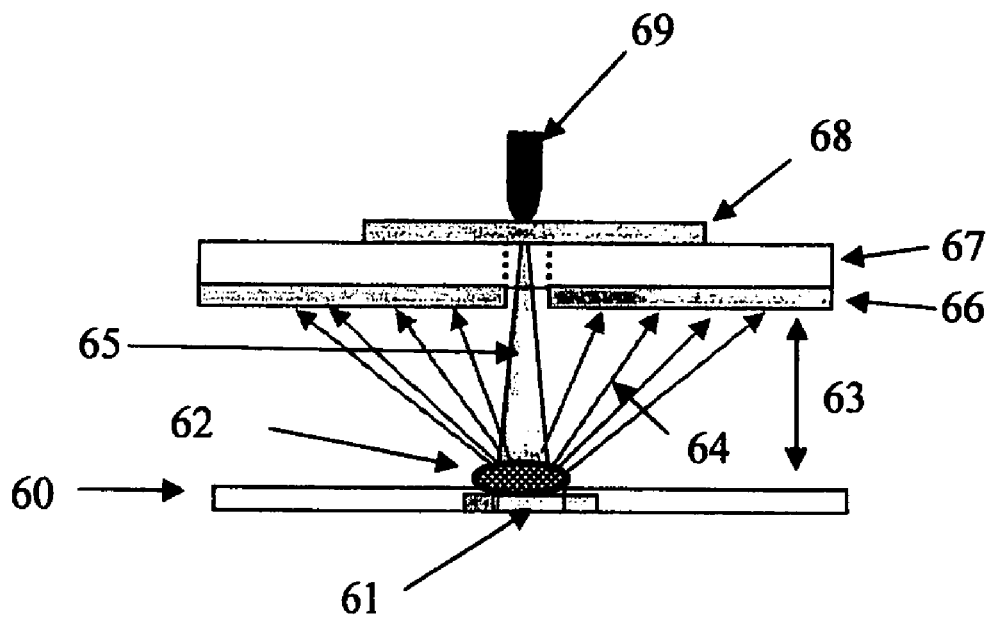
FIG. 7 shows an embodiment of the present invention which, like the design of FIG. 6, includes additional optical elements, in this instance a lens instead of a CPC.

Another fluorescent signal collection system in accordance with the present invention is shown in FIG. 7, where the CPC is replaced by a lens, 60 is the substrate material, and 61 is the fluorescent dye affixed thereon. The optical collection device in this embodiment is a lens 62, which directs the fluorescent signal 64 through filter 66 to the detector 67. The excitation light 65 comes from an LED 69, or other suitable optical source and illuminates the fluorophore after passing through a hole in the detector and then through filter 68 which serves to optically filter the excitation light so that the wavelength of the light impinging on the fluorophore coincides with the fluorophore excitation wavelength and photo-degradation is minimized (as described above). The collection efficiency of this system is again a function of the distance 63 between the fluorescent emitter and the photo-detector, but is less sensitive to this distance.

Figure 8:
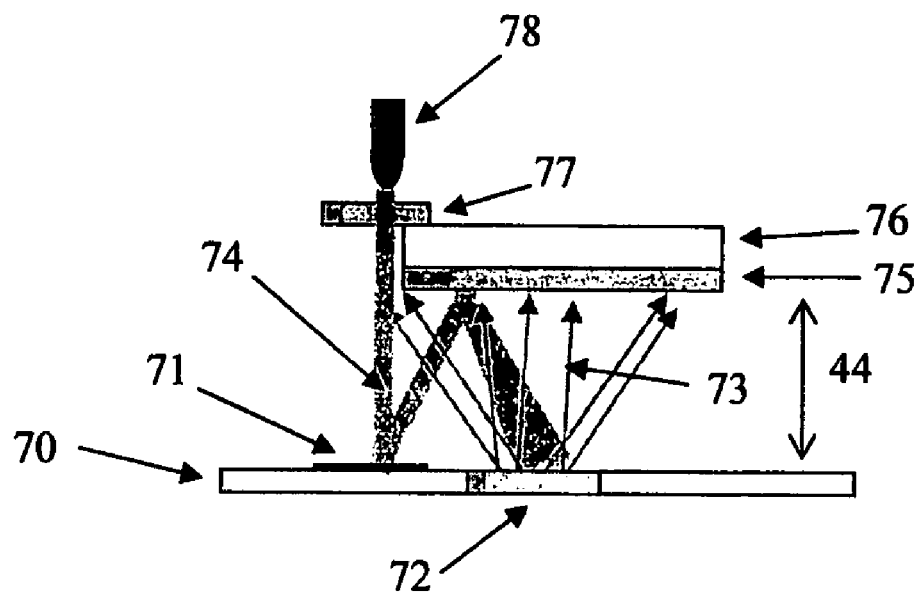
FIG. 8 shows another alternative design in accordance with the present invention where the illumination light is reflected off of the photo-detector's spectral filter.

FIG. 8 depicts yet another configuration in accordance with the present invention, where the illumination (excitation light) is reflected off of the photo-detector's spectral filter. In FIG. 8, the excitation light source 78 is tailored to match the dye's absorption spectrum (i.e., the excitation light wavelength which causes the dye to fluoresce) by filter 77 and is then propagated to reflector 71 which sends the light to the photo-detector's optical filter 75. The optical (i.e., spectral) filter's function is to reflect light that falls outside of the fluorescent signal's emission bandwidth, so that the excitation light is reflected by filter 75 and impinges on the fluorescent dye 72. The fluorescent dye 72 can be either directly deposited onto a substrate material 70 or the dye, pre-deposited on a bio-compatible plastic, is affixed to the bottom of 70 so that it is illuminated by the excitation light, and its fluorescent signal is captured by the photo-detector. As shown, the fluorescent signal 73 travels through spectral filter 75 before impinging upon the photo-detector 76.

Figure 9:
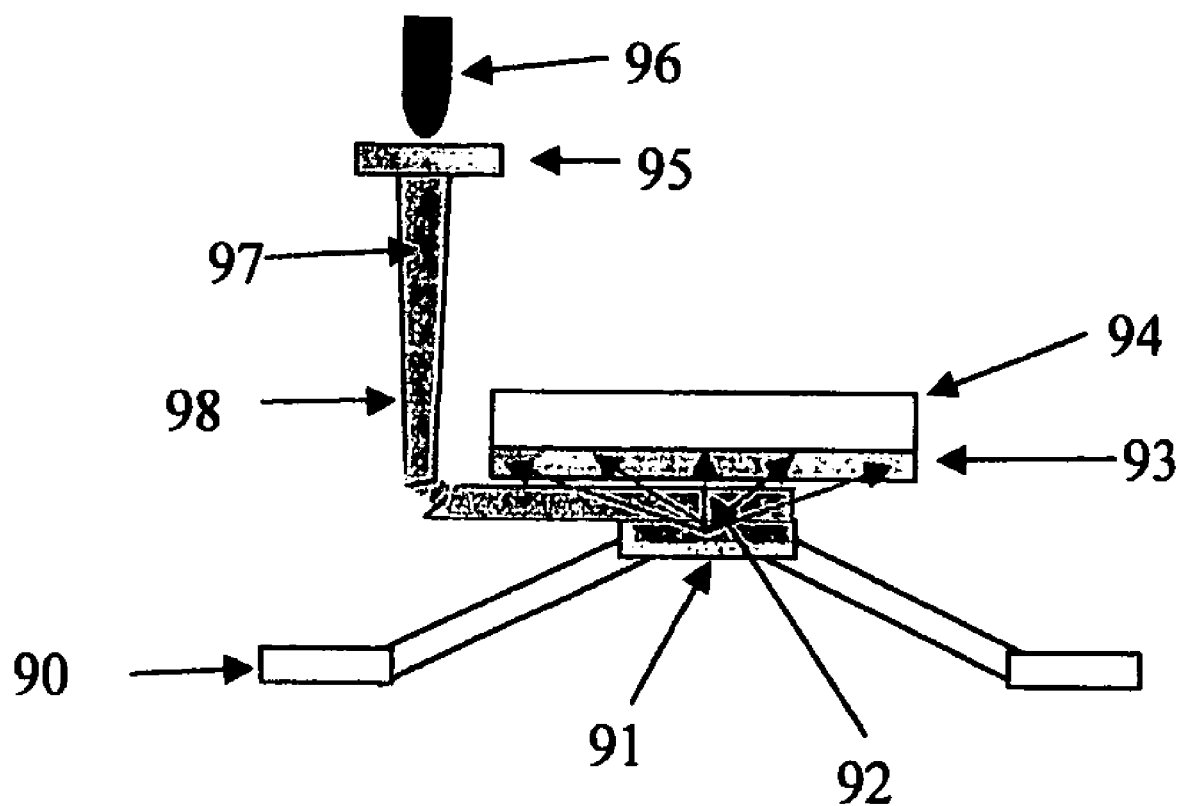
FIG. 9 shows a design in accordance with the present invention where the light from the excitation source is brought to the dye using an optical waveguide.

FIG. 9 shows another embodiment in accordance with the present invention where the light 97, from excitation source 96 is brought to the dye 91 using an optical waveguide 98 after being spectrally filtered by filter 95. The substrate 90 for the dye is again a suitable, preferably biocompatible material, as previously mentioned. In this embodiment, the excitation light is guided down the waveguide by total internal reflection to illuminate the dye spot. This delivers the excitation light to the dye spot due to the fact that the spot no longer supports total internal reflection, and the dye 91 absorbs at the excitation wavelength. The fluorescent signal 92 is also spectrally filtered by filter 93 before impinging on photo-detector 94. The advantage of this design is that while it effectively collects the emitted signal, it spatially decouples the delivery of the excitation light from the collection of the fluorescent signal.

Figure 10:
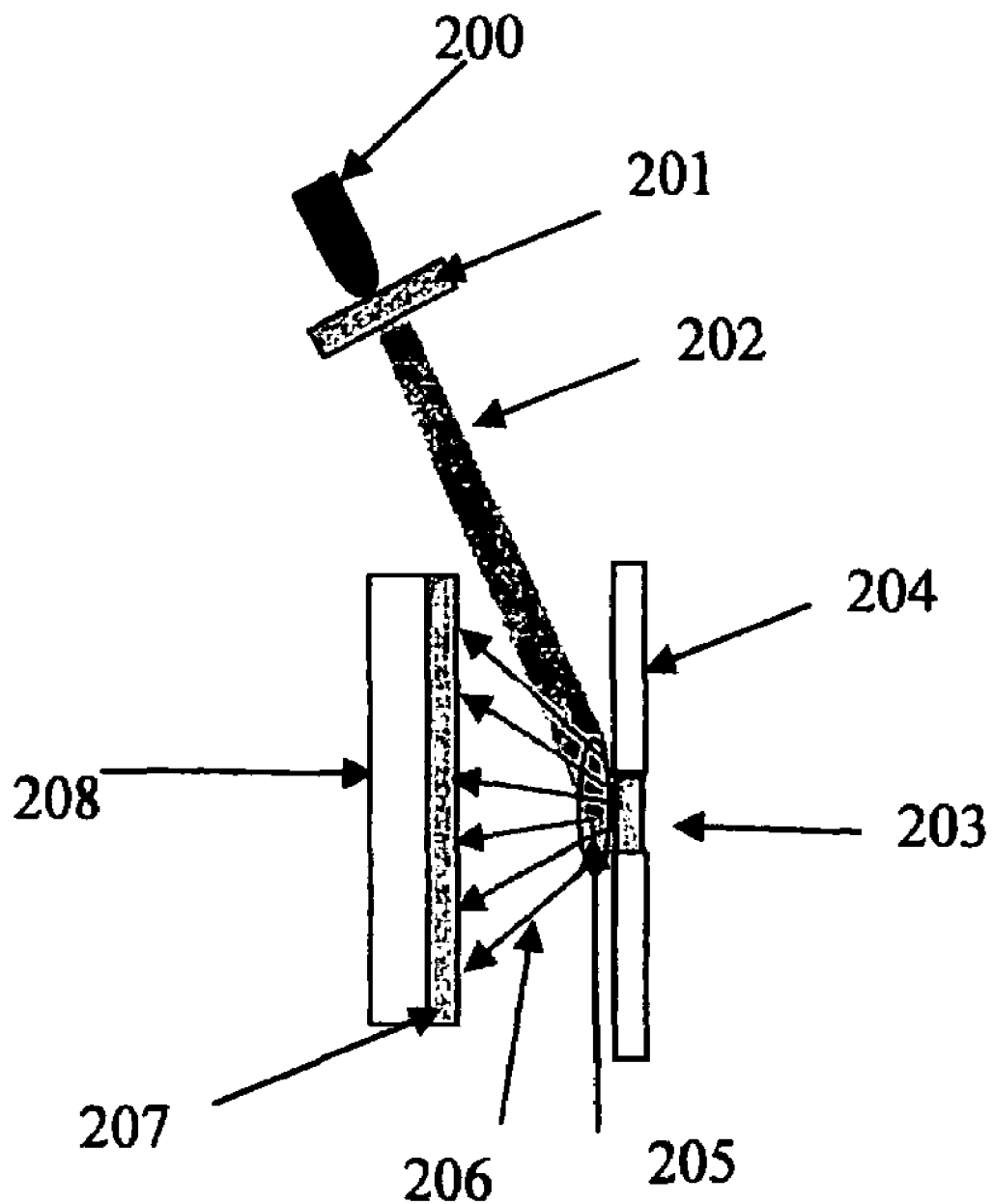
FIG. 10 shows an alternative orientation where the fluorophore and detector optics are rotated 90 degrees compared to the design shown in FIGS. 4 through 9.

FIG. 10 shows a preferred embodiment of the design where the detector and fluorescent dye assembly is rotated 90 degrees with respect to the illumination source. In FIG. 10, the light source 200 is spectrally filtered using a suitable dielectric or absorptive glass filter 201. The resulting excitation light 202 impinges upon an analyte sensitive dye 203. The dye spot is affixed to an animal derived product free, FDA and USP class VI compliant material 204. A lens 205 is used to help collect and direct the fluorescent light signal 206 towards another optical filter 207. This filter ideally only allows the fluorescent light to pass through and impinge upon the detector 208. As can be seen in FIG. 10, the excitation light beam path, the fluorophore and the photo-detector are not axially aligned. This can sometimes be advantageous in that the dimension of the photo-detector in at least one axis is not limited by the diameter of the port into which these optical elements are to be inserted, shown as 101 in FIG. 11.

In FIGS. 4 through 10, different apparatus configurations for the delivery of the excitation light and the collection of the fluorescent emission in accordance with the present invention are depicted. These various embodiments can be used in many applications in the, biotechnology, pharmaceutical, cosmetic, and food and beverage industries. These designs can also be used in waste water and chemical applications; where many of the sterility and bio-compatibility requirements can be relaxed or eliminated. It is to be understood that these configurations can also be used to detect the natural fluorescence of a target analyte without the fluorophore spot.

Figure 11:
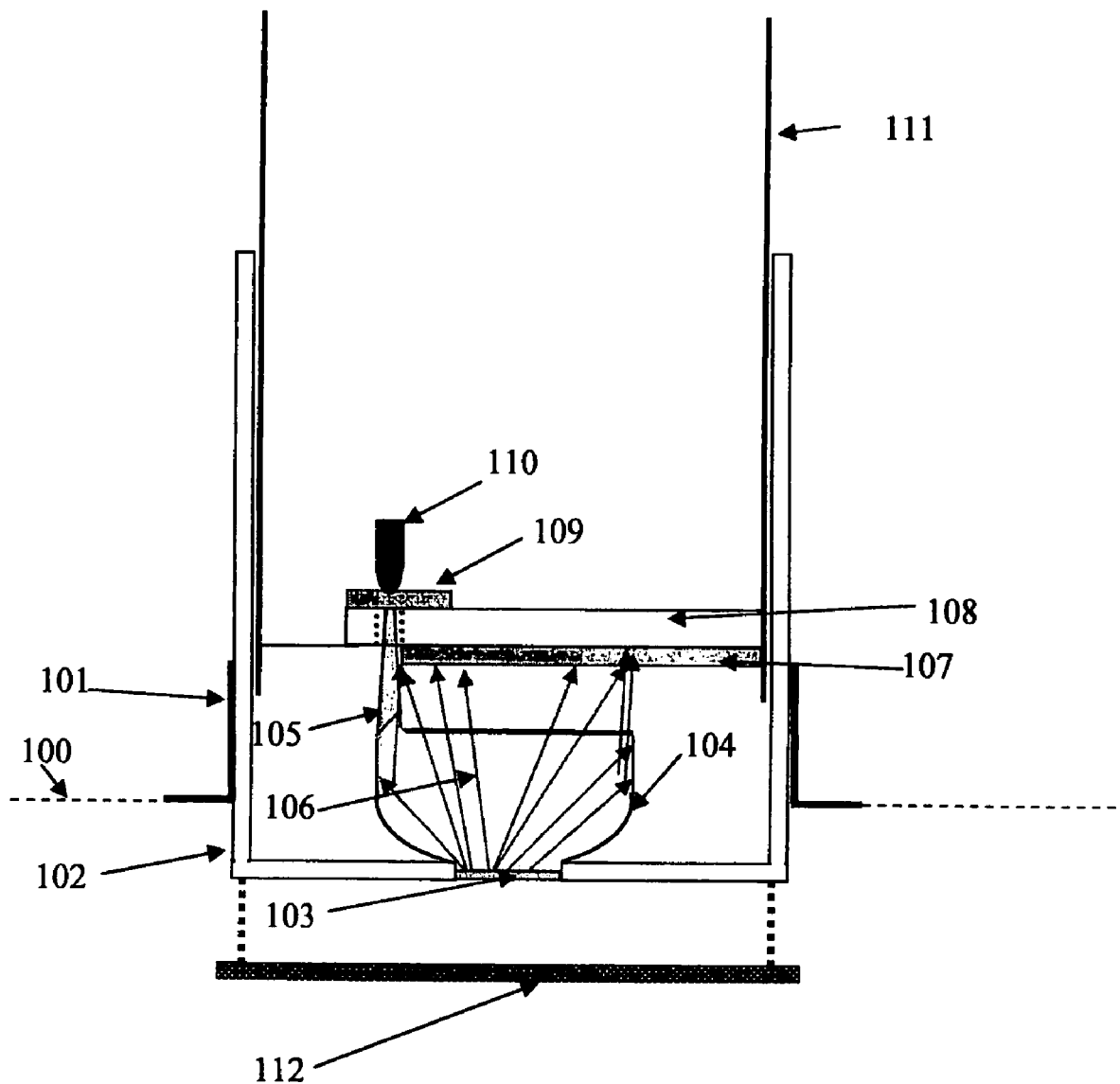
FIG. 11 depicts a system in accordance with the present invention by which any of the optical collection geometries previously shown can be employed in a sterile environment, for example in this Figure, by using a CPC.

In the majority of biotechnology, pharmaceutical and food applications, the analyte detection system needs to be contamination free and sterile before use. These constraints often lead to the use of disposable components. A disposable component in accordance with the present invention that can be used for phase fluorometry and that is compatible with the optical designs described in FIGS. 4-9 is shown in FIG. 11. This figure depicts a system by which any of the optical collection geometries shown in FIGS. 4 through 9 can be employed for use in a sterile environment. By way of example, in FIG. 11 a CPC similar to that used in FIG. 6 is shown. Here 100 is the lining of a disposable bioreactor or the wall of a standard fermentor and 101 is a port similar to the type used to house a standard electrochemical dissolved oxygen or pH probe. The disposable element 102 which is inserted into the port 101 is made of a bio-compatible, compliant material that is substantially free of leachable and/or extractable chemicals. An additional constraint for this material is that it be chemically, optically, and mechanically stable after sterilization, for which purpose≧25 kGy of gamma radiation doses or β- radiation are frequently employed. The optical excitation source 110 has its output light filtered by an absorptive glass filter or dielectric polymer filter 109. This filtered excitation light 105 is incident uniformly on the dye 103. The fluorescent signal 106 is collected by the CPC 104 and filtered by, for example, a glass or dielectric stack filter 107 before impinging on the photo-detector 108. Light shield 112 prevents ambient light from photo-degrading the dye during use. The insert 102 is designed to fit that no leakage occurs, and can suitably have fluorescent dye 103 affixed to it. The separation between the disposable elements and the non-disposable elements 111 is based on cost and convenience. In FIG. 10, the optics 104 used to enhance collection are part of the disposable elements, but this is not a necessary condition. In general, the filters 107 and 109, the excitation light source 110, and the photo-detector 108 will suitably remain in the non-disposable part of the device.

The design shown in FIG. 11 can also be implemented with traditional glass and steel bioreactors. In this case an adaptor and o-ring will normally be affixed to the probe in order to seal it into the bioreactor. This adaptor typically threads into the housing and seals the non-disposable probe body 111 into a head plate or side mount of the bioreactor. The disposable element 102 remains conceptually identical and allows the stainless steel or glass bioreactor to be equipped with disposable probes.

Figure 12:
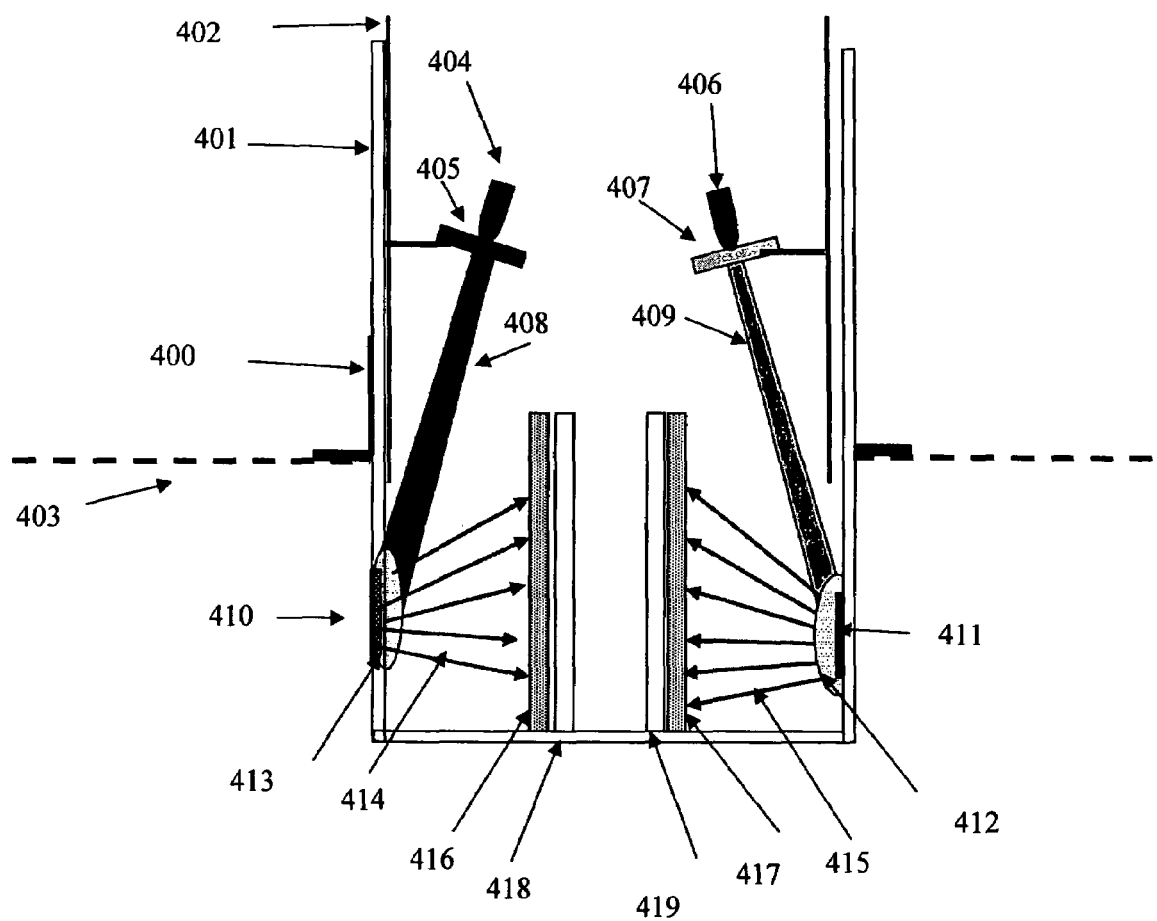
FIG. 12 shows a disposable optical sensor in accordance with the present invention which uses two physically distinct fluorophores to detect the analyte(s). The fluorophores can be the same or different.

FIG. 12 shows a port and disposable sensor assembly similar to that shown in FIG. 8 except that it utilizes two separate fluorophores. This assembly can also be used with an optical fiber based system, and can utilize a plurality of different fluorophores which can target different analytes of interest, or alternatively can target one analyte multiple times to thereby provide a redundant system. In FIG. 12, 400 is the port which is affixed to the disposable bioreactor liner 403. Component 402 (a "reader") housing the permanent optics and electronics (not shown) is inserted into a disposable sheath 401 which is made using a biocompatible material meeting all the aforementioned standards and requirements. The reader never comes in contact with the sterile contents of the bioreactor. In the reader, 404 is and LED or suitable light source which is optically filtered by 405. The filter 405 passes the excitation light 408 matching the first fluorophore 410. The emitted fluorescent signal 414 is collected by a lens 413 or other suitable optical train. The signal passes through optical filter 416 which substantially blocks all but the wavelengths emitted by the fluorophore. The signal light is converted to an electrical signal by the PIN photodiode or suitable photodetector 418. Similarly, another LED or suitable light source 406 is optically filtered by 407. The filter 407 passes the excitation light 409 matching the second fluorophore 411. The emitted fluorescent signal 415 is collected by a lens 412 or other suitable optical train. The signal passes through optical filter 417 which substantially blocks all but the wavelengths emitted by the fluorophore. The signal light is converted to an electrical signal by the PIN photodiode or suitable photodetector 419.

Figure 13:
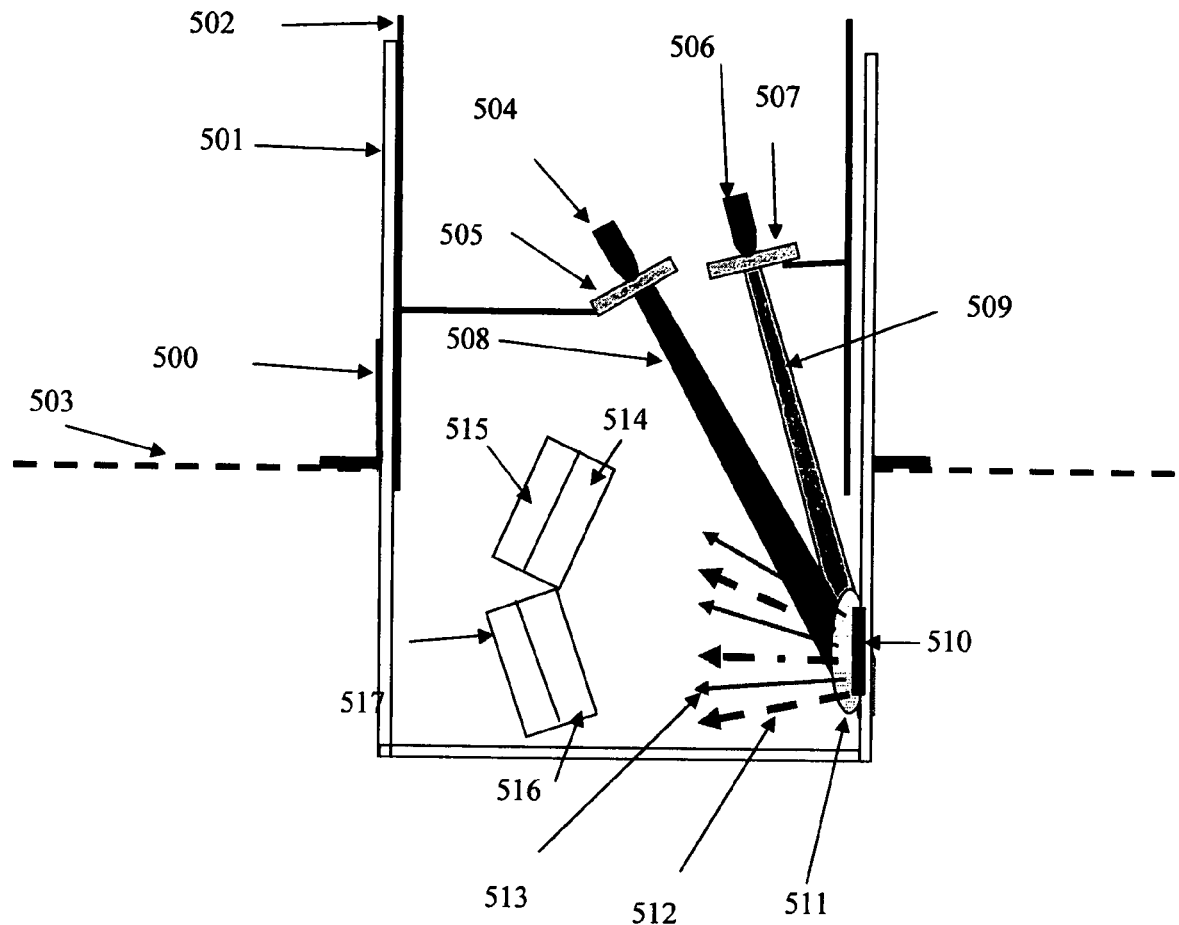
FIG. 13 shows a disposable optical sensor that uses a single spot that comprises multiple fluorophores. The excitation source can be a multiple wavelength source as shown, or it can be a single wavelength source.

FIG. 13 shows a system where the plural fluorophore spots are not physically separated. The spot can be made up of several regions containing different fluorophores, or all of the fluorophores can be evenly distributed over the entire area of the spot. This situation is analogous to detecting multiple natural fluorescent analytes within a sample. In FIG. 13, 500 is a port which is affixed to the disposable bioreactor or lining 503. The entire reader 502 housing the permanent optics and any requisite electronics (not shown) is inserted into a disposable sheath 501 which is made using a biocompatible material meeting all the aforementioned standards and requirements. The spot 510 which can contain multiple fluorophores uses a lens or other suitable optical system 511 to direct the multiple fluorescent signals 512 and 513 to multiple optical filters 514 and 516. These optical filters will typically allow only one of the emitted signals to pass through and will block the other. The signals fluorescent signals 512 and 513 can be detected using PIN photo-diodes or suitable photo-detectors 515 and 517. The fluorophore 510 can be illuminated by one or two appropriate light sources depending on the specific fluorophore or combination of fluorophores. In some cases multiple fluorophores embedded in a single matrix will have an absorption feature broad enough that only one light source will be required. FIG. 13 allows for the possibility of multiple sources (e.g.: appropriate LEDs) 504 and 506 supplying excitation light which is passed through optical filters 505 and 507 respectively. The filtered light 508 and 509 subsequently excites the fluorophore as discussed above. Although only two fluorophores are shown, this system can easily be generalized by the use of more than two fluorophores to detect N(N>2) target analytes.

The invention claimed is:

1. Optical system for the stimulation and collection of fluorescent signals emitted by a target fluorophore comprising:

i) a frequency modulated optical source which emits excitation light of a wavelength which will stimulate at least one target fluorophore to emit a fluorescent signal when illuminated by said excitation light;

ii) a first optical filter interposed between said optical source and said target fluorophore, said first optical filter substantially preventing radiation emitted by said optical source having a wavelength which will not stimulate said target fluorophore from impinging on said target fluorophore;

iii) a second optical filter interposed between said fluorophore and a photo-detector positioned to receive said emitted fluorescent signal, said second optical filter substantially preventing radiation other than said fluorescent signal from impinging on said photo-detector; and wherein said target fluorophore's cross sectional area is at least $\pi$ mm$^2$, wherein the beam path of at least one of the excitation light and the fluorescent signal is transmitted substantially through free space and wherein the collection efficiency provided by the optical system to said photo-detector is at least 50%.

2. An optical system in accordance with claim 1, wherein the beam path of the excitation light transmitted to the target fluorophore and the beam path of the fluorescent signal transmitted to the photo-detector are both substantially through free space.

3. An optical system in accordance with claim 1, wherein said target fluorophore is disposed on a bio-compatible, high optical transparency, animal derived product free, γ-radiation or β-radiation sterilizable substrate.

4. An optical system in accordance with claim 1, wherein said light source is an LED, diode laser or diode-pumped laser and wherein said photo-detector is a PIN photo-diode, avalanche photo-diode or a photomultiplier tube.

5. An optical system in accordance with claim 1, wherein each of said first optical filter and said second optical filter is independently a band pass filter comprising a multi-layer dielectric, an absorptive glass or a combination thereof.

6. An optical system in accordance with claim 1, wherein the optical source comprises Gallium Nitride.

7. An optical system in accordance with claim 1, which optical system includes a curved parabolic collimator or a lens which collects the fluorescent signal and directs said signal to the photo-detector.

8. An optical system in accordance with claim 1, wherein the excitation light is reflected by said second optical filter on to said target fluorophore or is directed to said target fluorophore via a slab optical waveguide.

9. An optical system in accordance with claim 1, wherein the excitation light source is mounted directly on the photo-detector.

10. An optical system in accordance with claim 1, wherein the excitation light is sinusoidally modulated.

11. An optical system in accordance with claim 1, wherein the wavelength of the excitation light is in the near ultraviolet.

12. An optical system in accordance with claim 1, wherein the excitation light has an intensity of no greater than about 3 µw/mm$^2$.

13. An optical system in accordance with claim 1, also comprising γ or β radiation sterilizable collection optics wherein said collection optics and said fluorophore are separable from said optical source, and said first and second optical filters.

14. An optical system in accordance with claim 1, wherein all three of the excitation light optical beam path, the fluorophore and the photo-detector are not axially aligned.

15. An optical system in accordance with claim 1, wherein said optical system further comprises at least a second source of excitation light and a plurality of fluorophores which fluorophores are physically separated.

16. A method for the stimulation and collection of fluorescent signals comprising the steps of:
  i) emitting from an optical source a beam of frequency modulated excitation light having a wavelength which will stimulate a target fluorophore having a diameter of at least 1 mm to emit a fluorescent signal when illuminated by said excitation light,
  ii) directing said excitation light onto a target fluorophore, after passing said excitation light through a first optical filter interposed between said optical source and said target fluorophore thereby causing said fluorophore to emit a fluorescent signal, said first optical filter substantially preventing any radiation emitted by said optical source having a wavelength which will not stimulate said target fluorophore from impinging on said target fluorophore,
  iii) directing said fluorescent signal to a photo-detector, said photo-detector having a second optical filter interposed between it and said fluorophore, said second filter substantially preventing radiation other than said fluorescent signal from impinging on said photo-detector, and
  iv) directing the output signal of said photo-detector to a data processor which calculates and displays the phase delay between said excitation light and said fluorescent signal, the beam path at least one of said excitation light and said fluorescent signal being substantially through free space and wherein said photo-detector collects at least 50% of said fluorescent signal.

17. The method of claim 16 wherein said data processor records said phase delay.

18. The method of claim 16 wherein at least one of said fluorescent signal and said excitation light is transmitted substantially through free space.

19. The method of claim 16 wherein said target fluorophore is disposed on a bio-compatible, high optical transparency, animal derived product free, γ-radiation or β-radiation sterilizable substrate.

20. The method of claim 16 wherein said first optical filter is a band pass filter comprising a combination of a multi-layer dielectric and absorptive glass.

21. The method of claim 16 wherein said excitation light is directed to said target fluorophore via an optical waveguide.

22. The method of claim 16 wherein said excitation light source is mounted directly on said photo-detector.

23. The method of claim 16 wherein the excitation light has an intensity of no greater than about 3 µW/mm$^2$.

24. The method of claim 16 wherein said fluorescent signal is collected and directed to the photo-detector using a curved parabolic collimator.

25. The method of claim 16, wherein all three of the excitation light optical beam path, the fluorophore and the photo-detector are not axially aligned.

* * * * *